(12) United States Patent
Arvinte et al.

(10) Patent No.: US 6,649,168 B2
(45) Date of Patent: Nov. 18, 2003

(54) PHARMACEUTICAL COMPOSITIONS COMPRISING TGF-BETA

(75) Inventors: Tudor Arvinte, Riehen (CH); Uwe Thomas Schote, Allschwil (CH); Juergen Sigg, Loerrach (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/953,722

(22) Filed: Sep. 17, 2001

(65) Prior Publication Data

US 2002/0064516 A1 May 30, 2002

Related U.S. Application Data

(63) Continuation of application No. PCT/EP00/02303, filed on Mar. 17, 2000.

(30) Foreign Application Priority Data

Mar. 17, 1999 (GB) .............................................. 9906060
Apr. 14, 1999 (GB) .............................................. 9908468

(51) Int. Cl.[7] ........................ A61K 39/00; A61K 38/00; A61K 47/00; C07K 14/00
(52) U.S. Cl. ........................ 424/198.1; 514/2; 514/769; 530/350
(58) Field of Search ...................... 424/198.1; 530/350; 514/2, 769

(56) References Cited

U.S. PATENT DOCUMENTS

| 4,455,256 A | 6/1984 | Urist .......................... 260/112 |
| 4,767,628 A | 8/1988 | Hutchinson .................. 424/426 |
| 4,942,035 A | 7/1990 | Churchill et al. ............ 424/423 |
| 4,962,091 A | 10/1990 | Eppstein et al. ................ 514/2 |
| 5,118,667 A | 6/1992 | Adams et al. .................. 514/12 |
| 5,158,934 A | 10/1992 | Ammann et al. .............. 514/12 |

(List continued on next page.)

FOREIGN PATENT DOCUMENTS

| DE | 196 47 828 A1 | 6/1997 |
| DE | 197 06 667 A 1 | 8/1998 |
| EP | 0 200 090 B1 | 12/1986 |
| EP | 0 200 341 A1 | 12/1986 |
| EP | 0 267 463 | 5/1988 |
| EP | 0 325 471 | 7/1989 |
| EP | 0 419 275 A1 | 3/1991 |
| EP | 0 510 913 | 10/1992 |
| EP | 0 585 168 A2 | 3/1994 |
| EP | 0 603 992 A1 | 6/1994 |
| EP | 0 616 814 A1 | 9/1994 |
| EP | 0 839 525 A1 | 5/1998 |
| EP | 0 845 269 A2 | 6/1998 |
| EP | 0 896 825 A1 | 2/1999 |
| WO | WO 89/11880 | 12/1989 |
| WO | WO 90/05522 | 5/1990 |
| WO | 0 433 225 A1 | 6/1991 |
| WO | WO 94/15653 | 7/1994 |
| WO | WO 94/16720 | 8/1994 |
| WO | WO 94/23740 | 10/1994 |
| WO | WO 95/27518 | 10/1995 |
| WO | WO 96/21427 | 8/1996 |
| WO | WO 96/27346 | 9/1996 |
| WO | WO 96/40183 | 12/1996 |
| WO | WO 97/21447 | 6/1997 |
| WO | WO 98/14478 | 4/1998 |
| WO | WO 98/16209 | 4/1998 |
| WO | WO 98/19697 | 5/1998 |
| WO | WO 98/31345 | 7/1998 |
| WO | WO 98/35631 | 8/1998 |
| WO | WO 98/35653 | 8/1998 |
| WO | WO 98/35703 | 8/1998 |
| WO | 197 09 763 A1 | 9/1998 |
| WO | WO 98/47485 | 10/1998 |
| WO | WO 98/51711 | 11/1998 |

OTHER PUBLICATIONS

Salomon Brothers, Orthopaedic and Trauma Markers, pp. 33–48 (1997).

Battler et al., "Intracoronary Injection of Basic Fibroblast Growth Factor Enhances Angiogenesis in Infarcted Swine Myocardium," JACC, vol. 22(7), pp. 2001–2006 (1993).

Holck et al., "Rate of Vascularization of Coralline Hydroxyapatite Spherical Implants Pretreated With Saline/Gentamicin, rTGF–β2, and Autogenous Plasma," Ophthalmic Plastic and Reconstructive Surgery, vol. 14(2), pp. 73–80 (1998).

Arvinte et al., "Comparative Study of Human and Salmon Calcitonin Secondary Structure in Solutions with Low Dielectric Constants," The Journal of Biological Chemistry, vol. 268(9), pp. 6408–6414 (1993).

Cudd et al., "Enhanced Potency of Human Calcitonin When Fibrillation is Avoided," vol. 84(6), pp. 717–719 (1995).

Pfeilschifter et al., "Modulation of type β transforming growth activity in bone cultures by osteotropic hormones," Proc. Natl. Acad. Sci., vol. 84, pp. 2024–2028 (1987).

Chen et al., "Influence of Calcium Ions on the Structure and Stability of Recombinant Human Deoxyribonuclease I in the Aqueous and Lyophilized States," Journal of Pharmacetuical Sciences, vol. 88(4), pp. 477–482 (1999).

Smith et al., "Calcium–mediated Thermostability in the Subtilisin Superfamily: The Crystal Sturcture of Bacillus Ak. 1 Protease at 1.8 Å Resolution," J. Mol. Biol., 294, pp. 1027–1040 (1999).

Derwent Publications Ltd., GB–London/AN 060919/XP 002144391 & JP 04 005965A, Abstract Jan. 5, 1992.

Chemical Abstracts 98–457732/199840, Niles, DE 197 06 667 A 1, Aug. 27, 1998.

Chemical Abstracts 98–496595/199843, Epple, DE 197 09 763 A 1, Sep. 17, 1998.

*Primary Examiner*—Lorraine Spector
*Assistant Examiner*—Janet L. Andres
(74) *Attorney, Agent, or Firm*—E. Jay Wilusz; John D. Thallemer

(57) ABSTRACT

This invention provides pharmaceutical compositions comprising TGF-β.

5 Claims, No Drawings

U.S. PATENT DOCUMENTS

| | | |
|---|---|---|
| 5,192,741 A | 3/1993 | Orsolini et al. ................ 514/4 |
| 5,192,743 A | 3/1993 | Hsu et al. ...................... 514/8 |
| 5,206,023 A | 4/1993 | Hunziker ................... 424/423 |
| 5,264,214 A | 11/1993 | Rhee et al. ................ 424/422 |
| 5,393,739 A * | 2/1995 | Bentz et al. .................. 514/12 |
| 5,445,832 A | 8/1995 | Orsolini et al. ............ 424/491 |
| 5,470,829 A | 11/1995 | Prisell et al. ................. 514/12 |
| 5,593,962 A | 1/1997 | Arvinte et al. ............... 514/12 |
| 5,595,760 A | 1/1997 | Cherif-Cheikh ............ 424/464 |
| 5,635,489 A | 6/1997 | Haley .......................... 514/21 |
| 5,665,428 A | 9/1997 | Cha et al. ................ 427/213.3 |
| 5,748,560 A | 5/1998 | Sawada ...................... 365/233 |
| 5,756,127 A | 5/1998 | Grisoni et al. .............. 424/489 |
| 5,766,618 A | 6/1998 | Laurencin et al. .......... 424/426 |
| 5,801,141 A | 9/1998 | Steber et al. ................... 514/2 |
| 5,854,207 A | 12/1998 | Lee et al. ....................... 514/2 |
| 6,156,330 A | 12/2000 | Tsukada et al. ............. 424/408 |

* cited by examiner

PHARMACEUTICAL COMPOSITIONS COMPRISING TGF-BETA

This is a continuation of International Application No. PCT/EP00/02303, filed Mar. 17, 2000.

The present invention relates to pharmaceutical compositions containing TGF-β.

Transforming growth factor-type β (TGF-β) is a homodimeric protein with a molecular mass of about 25,000 D. It denotes a family of multifunctional cytokines which regulate cell proliferation and differentiation processes, activity in bone and connective tissue. Highest levels of TGF-β are found in blood platelets and bone. The pharmacological effects of TGF-β are acknowledged in the art which may be promotion and acceleration of wound healing, bone, cartilage, and tissue repair, the treatment of cancer, bone marrow protective agent, mediator of cardioprotectin, anti inflammatory or immunosuppressive agent, mediator of inductive tissue interactions, induction of angiogenesis, oral mucositis, or growth regulator in mammalian cell cultures.

"TGF-β" as used therein are members of the TGF-β family. Any of the TGF-β isoforms and related molecules may be used in the pharmaceutical compositions of this invention. Preferred TGF-β of the present invention are TGF-β1, TGF-β2 and BMPs such as BMP 2 and BMP 7, especially TGF-β3. TGF-β3 is a 25 kD homodimeric, disulfide-linked protein composed of two 112 amino acid polypeptides containing 9 cysteines each. The cysteines of the homodimeric protein form 4 intrachain disulfide bonds and one interchain disulfide bond.

"TGF-β" embraces TGF-β mutants, e.g. TGF-β proteins exhibiting similar-biological activities and differing from the native TGF-β proteins by simple or multiple mutations, e.g. replacement, addition or omission of amino-acids.

We have found one problem in developing a dosage form containing TGF-β because of its poor physical and chemical stability in aqueous solution and in powder form. The poor stability may be observed when TGF-β is analyzed by chromatographic methods, such as gel electrophoresis and HPLC.

We have further found that in solution TGF-β binds to the walls of the container which constitutes a further problem. Such adsorption phenomena are major obstacles in the development of stabile aqueous formulations such as pre-filled gel bottles which are used more friendly for the patient and have reduced production costs. We have found for low therapeutical doses for TGF-β (e.g. below 10 μg/ml, e.g. between 0.001 and 10 μg/ml, e.g. between 1 and 10 μg/ml) the adsorption to surfaces has to be inhibited during the production of the dosage forms, during the storage and also before the use of the TGF-β formulation by the patient. The low concentrations used in formulations and the adsorption of TGF-β to surfaces impose also the development of highly sensitive analytical methods.

We have now found surprisingly that certain agents totally stop the adsorption of TGF-β to walls. Such agents may be used in different TGF-β dosage forms which have improved physical and chemical stability.

The present invention provides in one aspect a pharmaceutical composition comprising TGF-β and a water soluble salt chosen from calcium chloride, calcium phosphate, sodium acetate, potassium acetate, lithium acetate, ammonium acetate and ammonium bicarbonate, preferably calcium chloride and calcium phosphate.

The TGF-βs used in the water soluble salt pharmaceutical composition of the invention may be in the free form or in the form of their salts.

We have also developed an analytical method suitable for determining suitable concentrations of TGF-β, especially TGF-β3. When adsorption of a fluorescent molecule (protein) occurs to the cuvette walls the concentration of the molecule in the solution decreases. This change in concentration is monitored by changes (reduction) in the fluorescence intensity. With optimized slits in the excitation and emission monochromators the excitation beam is focused in a small region in the middle of the cuvette and the emission is collected also preferentially from the same region. This localized excitation and emission indicates that the contribution to the total emission intensity of chromophores which are bound to the cuvette walls to be minimal. In these conditions the fluorescence intensity is proportional to the concentration of the molecules in the aqueous solution (monitored in the middle of the cuvette). If binding occurs a decrease in the fluorescence intensity is observed. For TGF-β the intrinsic tryptophan fluorescence is used in the adsorption studies. To characterize an adsorption process the percentage from the total TGF-β in the cuvette which bound to the walls in a given time interval, e.g. 25 minutes, is measured. Fluorescence measurements are performed with a Spex Fluorolog® or a Spex Fluoromax® spectrophotometers with a stirred attachment in the cell holder at 25° C. Tryptophan fluorescence is excited at 280 nm and emission monitored at 340 nm. TGF-β is found to bind strongly to plastic, quartz and siliconised quartz cuvettes for a solution of TGF-β (1 μg/ml) in water. We have found a particularly good system for reproducibility of the majority of fluorescence adsorption studies if studies are performed in disposable plastic cuvettes (PMMA) supplied by Dispolob®, Kartell® P. N.1961.

A method to study protein adsorption to surfaces of different materials (other than the material from which the cuvettes are made) has also been developed. In these experiments TGF-β from a stock solution is added in a cuvette containing an aqueous solution (i.e. water, final TGF-β concentration 2 μg/ml) and the binding of TGF-β to the walls is monitored in time until the equilibrium state for the binding is reached (constant fluorescence intensity). Two sheets of the material needed to be studied are introduced in the cuvette and the changes in TGF-β3 fluorescence are monitored. If TGF-β is not binding to this material no change in time of the fluorescence intensity, i.e. no binding to the surface, is observed. If TGF-β3 binds to the new material a decrease in fluorescence intensity is measured.

In a preferred composition of the invention, the molar ratio of the water soluble salts ions to TGF-β, e.g. TGF-β3, is from 1:1 to 200:1, e.g. 10:1 to 100:1.

A man skilled in the art will appreciate that a wide variety of excipients may be used. For the water-soluble composition preferred components are e.g.:
  a) a liquid solvent, e.g. an alcohol, e.g. ethanol or isopropanol,
  b) a sugar or a sugar alcohol, e.g. mannitol, trehalose, sucrose, sorbitol, fructose, maltose, lactose or dextrans, preferably mannitol,
  c) other excipients, e.g. polygeline, polysorbate 20, PVC Palinode® C, and/or methyl-cellulose 4000 cP
  d) isotoning agents, e.g. sodium chloride,
  e) an acid, e.g. citric acid monohydrate, acetic acid, The amount of additives used can vary dependent on the intended use.

The water soluble pharmaceutical composition may comprise, e.g.
  0.05 μg/ml to 100 mg/ml of TGF-β3, e.g. 0.1 μg/ml to 40 mg/ml 0.1 to 200 mg/ml of the salt, e.g. calcium chloride, 1 to 90 mg/ml of a liquid solvent, e.g. an alcohol 1 to 50 mg/ml of sugar or sugar alcohol, 0.5 to 20 mg/ml of an acidic compound, e.g. citric acid monohydrate or acetic acid.

Such solutions may be used for standard ampoules, vials, pre-filled syringes or multiple administration systems.

If desired, a freeze dried formulation which may be stable for long periods of time, e.g. 6 months at 40° C., without the need for refrigerated storage, may be obtained from a TGF-β solution.

The freeze dried product may be obtained in conventional manner from a suitable solution, e.g. the above-disclosed solution, e.g. having a pH of from 1 to 4.5, e.g. from 2.5 to 4. Preferably, the concentration of TGF-β in this solution before freeze drying is from 0.1 µg/ml to 40 mg/ml, e.g. 10 µg to 2 mg/ml.

The freeze dried product may be re-dissolved into a solution which may be stable for long periods, e.g. up to 1 week, e.g. at pH below pH 5, e.g. between pH 2.5 and pH 4. In such a solution TGF-β is in the range of from 0.1 µg/ml to 40 mg/ml, e.g. 10 µg to 2 mg/ml.

The pH of the solutions may be from 2 to 10, e.g. from 2.5 to 4 and from 6.8 to 10.

The dried powder compositions, e.g. freeze dried products of the invention may be used for manufacturing of solutions of the ingredients, gels, creams, sprays.

A gel formulation according to the invention may comprise, e.g.

10 to 50 µg/ml of TGF-β3

0.1 to 10 mg/ml of the salt, e.g. calcium chloride, e.g. in a hydrated form 1 to 20 mg/ml of sugar or sugar alcohol, 5 to 30 mg/ml of a viscosity-increasing agent, e.g. methylcellulose 4000 cP.

0.5 to 10 mg/ml of an acidic compound, e.g. citric acid monohydrate or acetic acid.

The final pH of the gel may be between pH 3 and pH 4, e.g. pH 3.4 and pH 3.6.

A spray formulation according to the invention may comprise, e.g.

50 to 500 µg/ml of TGF-β3

1 to 20 mg/ml of salt, e.g. calcium chloride e.g. in a hydrated form 10 to 50 mg/ml of sugar or sugar alcohol, 1 to 20 mg/ml of an acid, e.g. citric acid monohydrate or acetic acid.

The final pH of the reconstituted spray solution may be between pH 3 and pH 4, e.g. between pH 3.2 and pH 3.6.

Despite the need to develop stable TGF-β dosage forms there still exists a need for effective delivery systems. One particular concern is that immediately after application TGF-β diffuses from the site of application. This effect is clearly not desired since TGF-β is a highly potent compound.

It was now surprisingly found that a composition comprising TGF-β and a biodegradable carrier, wherein the biodegradable carrier is a fibrillated calcitonin, e.g. a fibrillated calcitonin derivative, overcomes the above-mentioned concerns.

Therefore, in another aspect the present invention provides a pharmaceutical composition comprising TGF-β and a biodegradable carrier wherein the biodegradable carrier is fibrillated calcitonin.

Calcitonins are 32 amino acid polypeptide hormones with molecular weights around 3,500. They are secreted by the parafollicular cells of the thyroid gland in mammals and by the ultimobrachial gland of birds and fish.

In physiological saline solutions or buffers, particularly human calcitonin is not stable, it precipitates and forms gels which consist of calcitonin fibrils. Fibrillated calcitonin may be obtained by a process disclosed in EP 0 510 913, which is incorporated herein by reference. The concentration of calcitonin may be from 1 to 200 mg/ml, preferably from 5 to 100 mg/ml. Human calcitonin (hCT) fibrils have been characterized by electron microscopy [Bauer, H. H., Aebi, U., Häner, M., Hermann, R., Müller, M., Arvinte, T., Merkle, H. P. (1995) "Architecture and polymorphism of fibrillar supramolecular assemblies produced by in vitro aggregation of human calcitonin", Journal of Structural Biology 115, 1–15]. The time of fibrillation may be very well defined, e.g. from 5 minutes to 1 hour or 2 hours. Solutions of higher concentration fibrillate faster and fibrillation occurs faster at higher temperatures. Fibrillation may also depend on the ion content in the solution. It has been found that, for the fibrillation process to be completed, an incubation period of 1 hour is needed for a 200 mg/ml hCT solution in water. A double nucleation mechanism was proposed to explain human calcitonin fibrillation [Arvinte, T., Cudd, A., Drake, A. F.(1993) "The structure and mechanism of formation of human calcitonin fibrils", The Journal of Biological Chemistry 268, 6415–6422]. In the pharmaceutical compositions of this invention the fibrillated calcitonin may be used in the gel form. If desired, the calcitonin fibrils may be fragmented and then used as a dispersion of fragmented fibrils. A dispersion of fragmented fibrils may be obtained by a process disclosed in EP 0 510 913, which is incorporated herein by reference.

When used as a gel, the concentration of calcitonin may be from 1 to 200 mg/ml, preferably from 5 to 100 mg/ml. When used as a dispersion of fragmented fibrils the concentration of calcitonin may be up to 50 mg/ml.

In another aspect this invention provides a pharmaceutical composition comprising TGF-β and a fibrillated calcitonin wherein the calcitonin fibrils are formed in vivo at the application site.

The calcitonin is preferably human calcitonin (hCT) which may be synthetic or it may be produced by recombinant DNA technology. The term "human calcitonin" comprises not only natural human calcitonin, but also pharmaceutically acceptable derivatives and analogues thereof, e.g. those in which one or more of the amino acid groups occuring in the natural compounds are replaced or the N- or C-terminal group has been structurally modified. Salmon, eel or porcine calcitonin or derivatives thereof may also be used.

In a special aspect, this invention provides a pharmaceutical composition comprising TGF-β3 and a biodegradable carrier wherein the biodegradable carrier is fibrillated human calcitonin.

Human calcitonin may exist in the free form or in the form of a pharmaceutically acceptable acid addition salt. Such salts are known and their activity and compatibility are comparable to those of the free forms. Typical suitable acid addition salts are the hydrochlorides or acetates.

According to the present invention it has surprisingly been found that fibrillated calcitonin may be used in pharmaceutical compositions as a carrier for any pharmaceutically active agent or cells, e.g for the transplantation of cells in matrices in tissue generation. Accordingly, in another aspect the present invention provides pharmaceutical compositions comprising fibrillated calcitonin as a carrier.

In a further aspect the present invention provides the use of a fibrillated calcitonin as a carrier in pharmaceutical compositions.

The pharmaceutical compositions containing calcitonin may be obtained by mixing TGF-β, e.g. TGF-β3, with a solvent, e.g. a monoalkanol, e.g. methanol or ethanol, e.g. in an acidic environment, e.g. below a pH value of about 4, which may be filtered though a 0.2 μm filter prior to use (Acrodisc®, Gelman Science). The solution of TGF-β, e.g. TGF-β3, may be further admixed with a solution of calcitonin in e.g. citric acid buffer. The TGF-β, e.g. TGF-β3, solution and/or calcitonin solution and/or TGF-β, e.g. TGF-β3/calcitonin mixture may be used as such or in form of a lyophilisate.

The pharmaceutical composition containing calcitonin may contain further pharmaceutically acceptable excipients as conventional, e.g.

a) sugars or sugar alcohols, e.g. mannitol, sucrose, fructose, or trehalose;

b) salts, e.g. sodium chloride, calcium chloride, or magnesium chloride;

c) buffers, e.g. citrate, maleate, or phosphate;

d) cellulose derivatives, e.g. methyl cellulose;

e) antioxidants, e.g. ascorbic acid;

f) preservatives, e.g. benzalkonium chloride, or benzenthonium chloride.

The amount of additives used may vary dependent on the intended use. For example for obtaining more viscous calcitonin gels methyl cellulose in an amount of e.g. 0.5% by weight based on the total weight of the composition and sugars or sugar alcohols, usually in an amount of about 0.5% to 1% by weight based on the total weight of the composition may be used.

In another aspect the present invention provides a process for the production of a pharmaceutical composition comprising TGF-β, e.g. TGF-β3, and a biodegradable carrier wherein the biodegradable carrier is calcitonin, e.g. fibrillated calcitonin, which process comprises admixing a solution of TGF-β, e.g. TGF-β3, with a solution of calcitonin, e.g. fibrillated calcitonin.

TGF-β formulations of the invention may also be incorporated into an additional carrier or a support, e.g. a mechanical support. As support any bone substitute material such as ceramics materials in the form of granules or blocks, e.g. hydroxy apatite, tricalcium phosphate, coral derived materials or polymers, e.g. polylactide (PLA), e.g. a PLA sponge or e.g. collagen sponges, human bone derived orthopedic implants, metallic implants etc. may be used.

Suitable support materials may include tricalcium phosphate granules e.g. ChronOS® or Ceros® TCP produced by Mathys Ltd., Switzerland; Norian injectable cements marketed by Norian/Synthes, USA; porous bone graft substitute e.g. ProOsteon Implant 500® marketed by Interpore Int., USA; micro glass granules e.g. BiGran® marketed by Orthovita, USA; calcium phosphate e.g. Alpha BSM®, marketed by ETEX Corp., USA; calcium phosphate-based bone cement e.g. BoneSource®, marketed by Orthofix Inc., USA; gel, putty and flex forms e.g. Grafton DMB®, marketed by Osteotech Inc., USA; artificial formable bone matrix marketed by Bioapatite AB, Sweden; collagraft bone graft matrix, purified cow collagen and hydroxyapatite-tricalcium phosphate marketed by Zimmer Inc., USA; bovine skin collagen fibers coated with hydroxyapatite e.g. Healos® marketed by Orquest Inc., USA; collagen sponges e.g. Hemostagene® marketed by Coletica SA, France, or e.g. Helisat® marketed by Integra Life Sciences Inc., USA; bioresorbable polymer and bone cement e.g. OrthoDyn marketed by DynaGen Inc., USA; biodegradable POB/PBT copolymers marketed by IsoTis B. V., Netherlands; biodegradable polymers e.g. Prolease® and Medisorb® marketed by Alkermes, USA.

A suitable polylactide sponge for use in the pharmaceutical compositions of this invention may contain a ratio of the optically active L-form to the optically inactive DL-form of 80 to 20%, a pore size of 400 to 800 micrometers, a void of 70 to 80% and a molecular weight of 200,000 Dalton. It is non-toxic, well-tolerated by the organism and does not induce adverse reactions or is immunogenic. It is hydrolytically degraded into lactic acid which can be further metabolized.

A pharmaceutical composition comprising TGF-β, e.g. TGF-β3, fibrillated calcitonin and a support, e.g. a mechanical support, e.g. a biodegradable ceramic or polymer, is particularly useful for the treatment of larger bone defects where a mechanical strength of the composition is desired, e.g. if the composition has to span a relatively large distance between fractured bone.

The TGF-β, e.g. a TGF-β3/fibrillated calcitonin mixture may be added to the support, e.g. a PLA sponge, which may be sterilized with e.g. ethylene oxide and presoaked with e.g. either 25 μl ethanol 100% or with 25 μl buffered ethanol 20% (Fluka) prior to the loading with TGF-β, e.g. TGF-β3/fibrillated calcitonin mixture. Preferably, ethanol 100% is used. The loading solution may be put on the support, e.g. PLA sponge, when the support, e.g. PLA sponge, is still moist. After the loading the support, e.g. PLA sponge, may be dried with e.g. either $N_2$-gas for 1 minute at 25° C., or $N_2$-gas for 10 minutes at 25° C., or vacuum desiccator for 24 hours at 25° C., or vacuum oven for 24 hours at 30° C. Preferably $N_2$-gas for 10 minutes at 25° C. is used. Preferably, $N_2$-gas may be filtered through a 0.2 μm filter prior to use. Removing the loading solvent from the support, e.g. PLA sponge, causes TGF-β, e.g. TGF-β3, to get absorbed on the support, e.g. PLA sponge.

In a further aspect the present invention provides a process for the production of a pharmaceutical composition according to the present invention which process comprises incorporating a solution of TGF-β, e.g. TGF-β3, e.g. TGF-β3/calcitonin mixture, e.g. TGF-β, e.g. TGF-β3/fibrillated calcitonin mixture into a support, e.g. a polylactide (PLA) sponge.

The compositions of this invention are useful in the known indications of the particular active agent incorporated therein for the treatment of animals, particularly of mammals, and more particularly of human beings. These compositions are more particularly useful in the promotion and acceleration of wound healing, bone and tissue repair, e.g. spinal fusion or tendon repair, stroke, nerve repair, oral mucositis, the treatment of cancer, as a bone marrow protective agent, mediator of cardioprotectin, anti inflammatory or immunosuppressive agent, in transplantation, in the induction of angiogenesis, in heart surgery or infarcted heart, or as a growth regulator in mammalian cell cultures. In particular, the pharmaceutical composition of this invention are useful for, oral mucositis, the treatment of bone defects, for mediation of wound healing or induction of angiogenesis.

Calcitonin is a potent drug for the treatment of e.g. Paget's disease, some aspects of hypercalcaemia, and for postmenopausal osteoporosis. Calcitonins of different origins, mainly salmon, pig, eel and human are currently used therapeutically. Recently it was found that calcitonin fibrils per se are biologically active and may be used in treating calcium deficiency diseases. Accordingly, the physiological effect of fibrillated calcitonin may prove the pharmaceutical compositions of this invention to be even more advantageous when used in certain diseases, e.g. bone repair.

The exact amounts of the active agent and of the formulation to be administered depend on a number of factors, e.g. the type, severity and/or location of the defect and also on the age and general condition of the patient to be treated, the desired duration of treatment and the rate of release of active agent. The concentration of TGF-β, e.g. TGF-β3, may be from 0.1 μg/ml to about 100 mg/ml, preferably from 1 μg/ml to 50 mg/mi. About 1 μg to 10 mg of TGF-β, e.g. 0.1 mg to 5 mg, e.g. 1 mg of TGF-β3, has already a significant healing effect. Typically TGF-β, e.g. TGF-β3, is administered once in a single surgery.

The in vitro performance of the pharmaceutical compositions of the present invention may be investigated by, e.g. fluorescence measurements, aggregation and chemical stability.

The in vivo performance of the pharmaceutical compositions of the present invention may be tested on horses (wound healing), pigs (oral mucositis inhibition), rabbits e.g. with the rabbit cranial defect model (induction of repairing of bone defects), and femal mice (induction of angiogenesis).

EXAMPLE 1

Aggregation of TGF-β3 in different aqueous conditions is studied using 90°-lightscattering. Using the same wavelength for excitation and emission, e.g. excitation and emission wavelength is 560 nm, a Spectrofluorimeter is used to detect aggregation events by measuring the 90°-light scatter. In this method a small aliquot of TGF-β3 stock solution is added in the fluorescence cuvette. If aggregation takes place an increase in the 90°-light scatter intensity is observed. If the solution in which TGF-β is added does not induce aggregation no increase in the light scatter intensity is observed.

A composition comprising 10 mM calcium chloride or 10 mM calcium phosphate, and 20% isopropanol or ethanol is prepared. No aggregation is observed with increasing TGF-β3 concentration up to 60 μg/ml TGF-β3.

EXAMPLE 2

The chemical stability of lyophilized formulation in vials containing TGF-β3, 5.881 mg of $CaCl_2$ and 25 mg of mannitol have been tested. The vials are solubilized to obtain TGF-β3 solutions of 0.1 mg/ml and 0.25 mg/ml. TGF-β3 by-products (related substances) are determined by capillary zone electrophoresis. The results show that the $CaCl_2$ formulation is very stable chemically. There is no increase in the TGF-β3 by-products after 6 month incubation at 40° C. In comparison, in the absence of $CaCl_2$ the chemical degradation is substantial.

EXAMPLE 3

The lyophilized powder in the vial contains TGF-β3, mannitol, $CaCl_2$. It is solubilized with a solvent containing citric acid, sodium hydroxide (up to pH 3.4) and water. After solubilization the gel is formed by adding a carrier which consisted of methylcellulose 4000 cP, mannitol and water. The concentrations in the final gel solution are: 25 μg/ml TGF-β3, 9.85 mg/ml mannitol, 1.470 mg/ml $CaCl_2.2H_2O$, 2.103 mg/ml citric acid monohydrate, 16.5 mg/ml methylcellulose 4000 cP. The final pH of the gel is pH 3.5±0.1.

EXAMPLE 4

The lyophilized powder in the vial contained: TGF-β3, mannitol and $CaCl_2$. It is solubilized with a solvent consisting of citric acid buffer, pH 3.8 (adjusted with sodium hydroxide). The concentrations in the final spray solution are: 250 μg/ml TGF-β3 (for the spray the TGF-β3 concentration is 10 times higher than for the gel since the volume applied from the spray is 10 times smaller than the applied gel volume), 25 mg/ml mannitol, 5.881 mg/ml of $CaCl_2•2H_2O$ and 8.41 mg/ml citric acid monohydrate. The final pH of the reconstituted spray solution is between pH 3.2 and pH 3.6.

EXAMPLE 5

The TGF-β3/$CaCl_2$ gel and spray formulations of examples 3 and 4 respectively are applied on horses for these trials.

The results are reported in the following table (median wound area in $cm^2$):

|  | Ca-gel | Ca-spray |
|---|---|---|
| 1st day | 363 | 554.0 |
| After 2 months | 24 | 0 |

The clinical evaluation of the scar formation of extremity wounds four months after surgery are (scoring of scar formation: 0=minimal, 1=medium, 2=high):

|  | Ca-gel | Ca-spray |
|---|---|---|
|  | 0.562 | 0.375 |

EXAMPLE 6

A TGF-β3/$CaCl_2$ formulation is tested onto the buccal mucosa of pigs. The composition used is prepared from a lyophilized formulation containing TGF-β3, $CaCl_2$ and mannitol, which is solubilized with a glycine buffer. The solution applied contains 25 μg/ml of TGF-β3, 2.5 mg/ml of mannitol, 80 mM of $CaCl_2$ (0.588 mg/ml $CaCl_2•2H_2O$), glycine buffer pH 3.0 (0.6 mg/ml glycine, pH adjusted with HCl) and 6.4 mg/ml of methylcellulose 4000 cP.

Cell proliferation is measured by the BrdU (5-bromo-2'-deoxyuridine) assay. Punch biopsies of the buccal mucosa are processed, sectioned and stained with a monoclonal antibody against BrdU in order to identify DNA synthesis in individual cells.

The results show that TGF-β3/$CaCl_2$ formulation applied on in vivo pig model induces a strong reduction in the basal cell proliferation rate.

EXAMPLE 7

TABLE 1

Effect of a pharmaceutical composition comprising TGF-β3 (50 μg/sponge, corresponding to 0.3 μg/$mm^3$), fibrillated human calcitonin (hCT) (50 μl human calcitonin gel, corresponding to a concentration of 30 mg/ml, corresponding to 1.5 mg/sponge) and a polylactide (PLA) sponge (disk of a diameter of 8.3 mm) in the rabbit cranial defect model.

|  | effect (expressed as pixels × $10^4$ per burr hole) |
|---|---|
| Control (PLA sponge alone) | 2.5 |
| PLA sponge + hCT gel | 2.0 |
| PLA sponge + hCT gel + TGF-β3 | 10.5 |

Table 1 shows the effect of an empty PLA sponge, compared to a PLA sponge with hCT fibrils, compared to a PLA sponge with hCT fibrils and TGF-β3 in the rabbit cranial defect model. Bone disks removed for creation of the defect served as controls for the extent of bone regeneration. After an eight week healing period the bony filling of the defects was determined by quantitative radiography. The total defect area corresponded to 113320.2 pixels and was taken as 100% for further calculations. Accordingly, complete regeneration corresponded to a value of $11.3 \times 10^4$ pixels.

The results show that treatment with TGF-$\beta$3 induces strong bone formation. Insignificant repair occurs in the animal group without TGF-$\beta$3.

The pharmaceutical compositions of this invention comprising fibrillated calcitonin induce a rapid bone wound healing. Moreover, diffusion and/or systemic effect of TGF-$\beta$, e.g. TGF-$\beta$3 are prevented.

EXAMPLE 8

Table 2 shows the effect hCT fibrils, compared to hCT fibrils plus TGF-$\beta$3 in the subcutaneous mouse model.

TABLE 2

Effect of a pharmaceutical composition comprising TGF-$\beta$3 (2.5 µg/ml) and fibrillated calcitonin (50 mg/ml) in the mouse subcutaneous model.

| | vascularized area (expressed as mm$^2$ after 17 days) |
|---|---|
| Control (no treatment) | 13.9 |
| human calcitonin gel | 13.9 |
| human calcitonin gel + TGF-$\beta$3 | 31.1 |

The results show that treatment with TGF-$\beta$3 induces strong vascularization in the animal group treated with TGF-$\beta$3.

The pharmaceutical compositions of this invention comprising fibrillated calcitonin induce a rapid bone wound healing or vascularization. Moreover, diffusion and/or systemic effect of TGF-$\beta$, e.g. TGF-$\beta$3 are prevented.

What is claimed is:

1. A pharmaceutical dry powder composition comprising a TGF-$\beta$ in a water soluble salt chosen from calcium chloride, calcium phosphate, potassium acetate, lithium acetate, ammonium acetate and ammonium bicarbonate.

2. A method of administering the pharmaceutical composition of claim 1 comprising the steps of adding said pharmaceutical composition to a liquid solvent to create a liquid form of said pharmaceutical composition and administering said liquid form to an animal in need thereof.

3. A process for the preparation of a pharmaceutical composition according to claim 1 which process comprises admixing a TGF-$\beta$ with a salt selected from the group comprising calcium chloride, calcium phosphate, potassium acetate, lithium acetate, ammonium acetate and ammonium bicarbonate.

4. A process of the preparation of a pharmaceutical composition according to claim 3 which process comprises further incorporating the composition into a support.

5. A method of treatment comprising administering a pharmaceutical composition according to claim 1 for initiation of a therapy selected from the following: promotion and acceleration of wound healing, repair of bone, soft tissue, stroke, and nerves, treatment of cancer, induction of bone marrow protection, mediation of cardioprotection, induction of anti-inflammatory activity, induction of immunosuppressive activity, regulation of mammalian cell growth and induction of angiogenesis.

* * * * *